United States Patent
Bailey et al.

(10) Patent No.: US 8,595,025 B2
(45) Date of Patent: Nov. 26, 2013

(54) METHOD FOR ROUTING USER SERVICE REQUESTS FROM A TELEMEDICINE STATION

(75) Inventors: Kenny B. Bailey, Folsom, CA (US); David Poisner, Carmichael, CA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 976 days.

(21) Appl. No.: 11/902,794

(22) Filed: Sep. 25, 2007

(65) Prior Publication Data

US 2009/0083066 A1    Mar. 26, 2009

(51) Int. Cl.
*G06Q 10/00* (2012.01)
*G06Q 50/00* (2012.01)

(52) U.S. Cl.
USPC .................................... 705/2; 705/3

(58) Field of Classification Search
USPC ........................................ 705/2–3; 600/300
See application file for complete search history.

(56) References Cited

U.S. PATENT DOCUMENTS

| 7,430,290 | B2 * | 9/2008 | Zhu ........................ 379/265.01 |
| 2005/0065821 | A1 * | 3/2005 | Kalies, Jr. ...................... 705/2 |
| 2006/0195339 | A1 * | 8/2006 | Backhaus et al. ................ 705/2 |
| 2008/0139889 | A1 * | 6/2008 | Bagan ........................ 600/300 |
| 2008/0147741 | A1 * | 6/2008 | Gonen et al. ............... 707/104.1 |
| 2009/0048712 | A1 * | 2/2009 | Rosenblum ................... 700/242 |

* cited by examiner

*Primary Examiner* — Luke Gilligan
(74) *Attorney, Agent, or Firm* — Pillsbury Winthrop Shaw Pittman LLP

(57) ABSTRACT

A station such as a telemedicine booth may send a request for medical service to a routing agent, which may route the request for medical service to a medical service provider. The routing may be based on one or more routing criteria, such as for example medical parameters of a user collected at the station and sent to the routing agent, location of a user, or quality of service indicators.

3 Claims, 4 Drawing Sheets

METHOD FOR ROUTING USER SERVICE REQUESTS FROM A TELEMEDICINE STATION

FIELD OF THE INVENTION

The present invention generally relates to the field of providing medical services to users located remotely from medical service providers.

BACKGROUND OF THE INVENTION

Advances in computing and communications technology have allowed increasing remote operations in many fields. Among other fields, these technologies have enabled the remote provision of medical services to locations where a user may not have immediate in-person access to a medical services professional.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
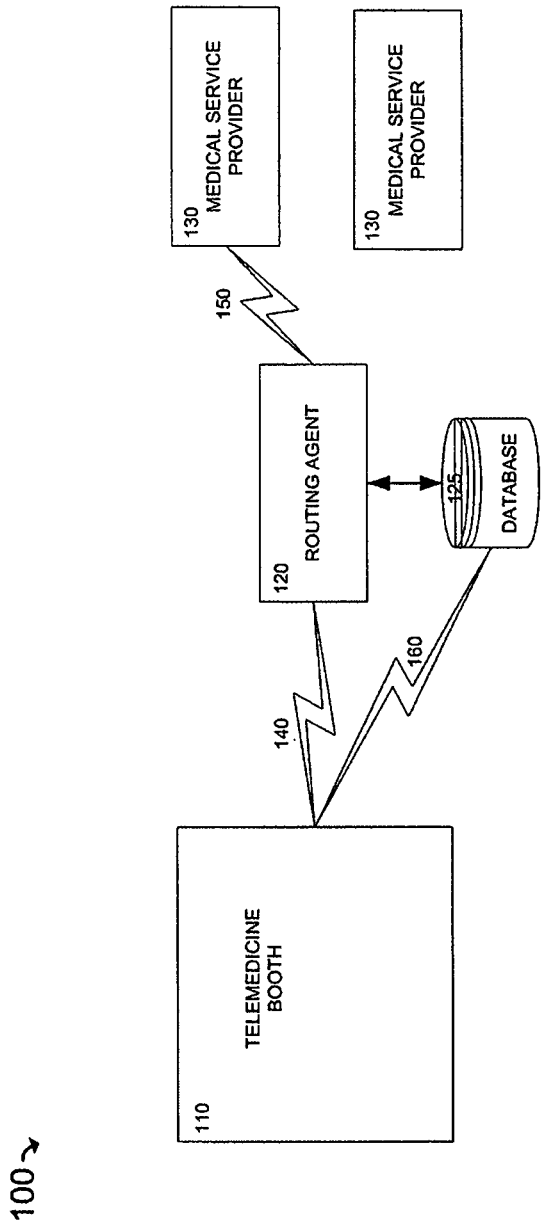
FIG. 1 is a block diagram of a system for routing a medical service request according to an embodiment of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the system's registers and/or memories into other data similarly represented as physical quantities within the system's memories, registers or other such information storage, transmission or display devices. In addition, the term "plurality" may be used throughout the specification to describe two or more components, devices, elements, parameters and the like.

As used herein, medical parameters of a patient or user may refer to a user's physical characteristics such as for example weight, height, pulse, respiration rate, and blood type and or symptoms such as for example a cough, fever, stuffy nose, and nausea. Other characteristics may be included, and other information may be included, such as images (e.g., images of a portion of skin, or of the patient). In some instances, obtaining the current status of a user's medical parameters may require equipment or a system for data capture. For example, a thermometer may be required to capture a user's body temperature, or a camera may be required to view a skin sample. In some instances, a user may be able to describe his symptoms or other medical parameters verbally or by entry in a computerized or other user interface.

As used herein, a request for medical service may include a question, concern, request, report, or other request for diagnosis or treatment of a user's medical condition or health. A patient or user may have one or more reasons for requesting medical service. In some instances the user's condition may be pre-existing and require monitoring. In other instances, the user's condition may not be known and may require capture of medical parameters to facilitate a diagnosis by a medical services provider. In still other instances, a user may be aware of certain symptoms and may seek to identify possible causes of the symptoms. Other reasons for requesting medical service may also be addressed.

As used herein, a medical consultation may be or include a dialogue, discussion, transferal of patient or user personal information and or medical records to a medical service provider or medical agent for the purpose of fulfilling a request for medical services. The consultation may include discussion or investigation of a user's medical history, current medical parameters such as e.g. symptoms, medical care preferences, and other parameters used in medical consultations as known in the art. Further, in some embodiments, the medical consultation may include one or more of referral to another medical service provider, dispensation of a prescription, dispensation of medicine, instructions for self-care and the like.

Reference is now made to FIG. 1 which shows a system 100 for routing a medical service request according to an embodiment of the invention. The simplified components schematically illustrated in FIG. 1 are intended for demonstration purposes only, and other or additional components may be used.

Telemedicine station or booth 110 may be for example an enclosure or enclosed booth capable of operations required for routing a user's request for medical service. Other structures or stations, such as a set of components mounted to an open or not enclosed structure, may be used. These operations may include for example authenticating a user identification, authorizing a user for payment, capturing user medical parameters, contacting a routing agent, sending captured medical parameters to the routing agent, and enabling the user to communicate with a medical services provider. In some embodiments, telemedicine booth 110 may also be capable of dispensing medicine or prescriptions as directed by the medical services provider. Telemedicine booth 100 may also be capable of other operations associated with routing a user's request for medical service. Routing agent 120 may be a system or device capable of collecting a user's medical parameters from telemedicine booth 110, routing the user's request for medical services to a medical services provider, and establishing a link between the user and a medical services provider such as medical services provider 130. Routing agent 120 may also be capable of or assist in authenticating the identity of a user in telemedicine booth 110 and/or authorizing a user to use system 100. Routing agent 120 may be or include a computer, computerized systems, or other equipment and may be operated, monitored, or staffed by for example a healthcare consultant or other personnel trained to route medical service requests using the resources of routing agent 120. In some embodiments, routing agent 120 may include a terminal or equipment for use by a healthcare consultant to communicate with telemedicine booth 110, a user in telemedicine booth 110, and/or one or more medical service providers 130. Other equipment and functions may also be provided.

In some embodiments, telemedicine booth 110 may be able to initiate a communications link 140 with routing agent 120. Communications link 140 may be one or more of an audio link, a video or videoconference link, and/or a data link and may utilize one or more of a wired, wireless, cellular telephone, or satellite medium as known in the art. Activation of communications link 140 may be initiated by the user or as a result of a process, procedure, or operation such as the user entering telemedicine booth 110, entry of a credit card or identification card, or confirmation of payment. Other operations for activating communication link 140 may also be used.

Using communications link 140, user information from telemedicine booth 110 may be transferred to routing agent 120. In some embodiments, information may be transferred as a result of data captured from the user such as for example medical parameters or identification at telemedicine booth 110 or by a conversation on for example an audio or video link or a text communication link. Other techniques for transferring user information from telemedicine booth over communications link 140 may also be used. In some embodiments, information transfer over communications link 140 may also be two-way to enable routing agent 120 to provide instructions, to ask questions, or provide other information to a user in telemedicine boot 110.

Routing agent 120 and/or telemedicine booth 110 may be connected locally or remotely to one or more databases 125 for storing records. Database 125 may be or include any suitable software process or application and memory for storing and retrieving information, files, or a plurality of documents, such as a database system such as, e.g., a relational database. Items stored in database 125 may include for example personal data regarding identity, patient medical records, credit or payment status, and or other records related to the provision of medical services for users and/or patients. Additional items stored in database 125 may include information on medical service providers such as for example location, medical specialty, availability, fees, ratings, and the like. In some embodiments, different categories of information such as e.g. user records and medical service provider records may be stored in a number of databases 125. Routing agent 120 may use information stored in one or more databases 125 for one or more of verifying a user's identity, credit or payment, and/or routing a user's request for medical service to a medical service provider or medical agent. In some embodiments, telemedicine booth 110 may establish a communications link 160 with database 125 directly for authenticating a user's identity and/or authorizing a user's payment type, e.g. credit card, debit card, or account based payment. In some embodiments, medical service provider 130 may establish a communication link with database 125 for accessing a user's personal information, medical records, or medical parameters.

Database 125 may include a recordkeeping system for access to medical records such as e.g. retrieving or updating medical records. Such a recordkeeping system may include activity logging to comply with relevant patient privacy or other requirements or regulations and may for example record the name of agents and/or medical service providers, time of access, type of access, and the like.

In some embodiments, routing agent 120 may, with user information collected from telemedicine booth 110 and one or more databases 125 and with medical service provider information collected from one or more databases 125 determine one or more medical service providers 130 of a plurality of medical service providers to which a user's request for medical service should be routed or connected. Routing agent 120 may establish a communications link 150 between routing agent 120 and medical service provider 130 by possibly the same or different communications technology as that for communications link 140. In some embodiments communications link 150 may also have the same capabilities for data transfer and two-way communications as communications link 140; however in other embodiments the links may differ in type and capability. Once communications link 150 is established, routing agent 120 may, in some embodiments, transfer communications link 150 to telemedicine booth 110, connect communication links 140 and 150, or establish a separate direct link between telemedicine booth 110 and medical service provider 130.

Medical service provider 130 may be or include a licensed medical service professional such as for example a doctor, nurse, nurse-practitioner, or dentist who is available to accept a request for medical service from a user at telemedicine booth 110 and provide a medical consultation via a communication link established by routing agent 120 between medical service provider 130 and telemedicine booth 110. Other providers may be used, depending on need, licensing, or convention. User information captured at telemedicine booth 110 and/or retrieved from database 125 may be transferred to medical service provider 130 before or during a medical consultation. Medical service provider 130 may be capable of and authorized to dispense medicine, prescriptions, and/or directions for care remotely to a user at telemedicine booth 110.

It is believed that the combination of features in the various embodiments of the system and method of the present invention is novel. For example, no device known to the inventors today can provide a combination of capturing user medical parameters, contacting a routing agent, routing a request for medical service to a medical service provider based on one or more routing criteria, establishing a link between the telemedicine station and the medical service provider, and optionally dispensing medicine at the telemedicine booth as directed by the medical services provider. Other novel features and combinations of features are described herein.

Figure 2:
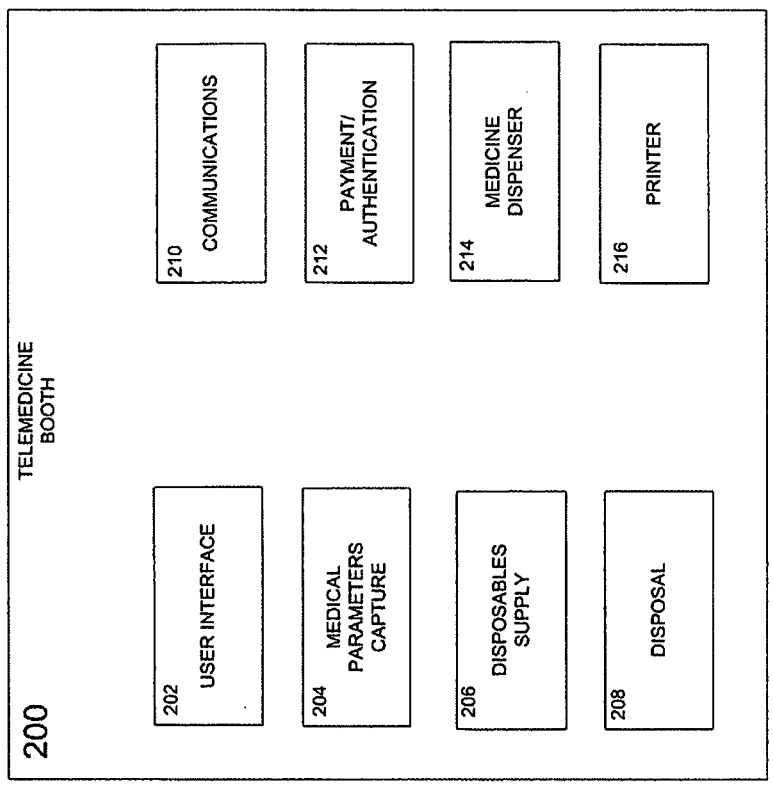
FIG. 2 is a schematic illustration of a telemedicine station according to an embodiment of the invention.

Reference is now made to FIG. 2, a telemedicine station or booth 200 according to an embodiment of the invention. Telemedicine booth 200 may be the same as telemedicine booth 110 of the embodiment of FIG. 1 and may include for example a user interface 202, a medical parameters capture system 204, a disposables supply 206, a disposal system 208, a communications system 210, a payment/authentication system 212, a medicine dispenser 214, and a printer 216. Other systems, devices, and/or components may also be included. Telemedicine booth 200 may be a complete enclosure with a closable door that may allow a user to have privacy during a medical consultation. Furthermore, telemedicine booth 200 may be self contained and or capable of being placed in a number of locations such as for example in a shopping mall, work location, village, and other remote locations. In other embodiments, telemedicine station or booth 200 need not be an enclosed structure.

User interface 202 may be or include any interface known in the art for providing two-way communications between a user and telemedicine booth 200. A user may communicate with telemedicine booth 200 in verbal, visual, text entry, or other forms. Telemedicine booth 200 may communicate with a user through an audio, video and/or textual medium. Consequently user interface 202 may include one or more of a display screen, computing device, telephone, video camera, touch-screen, speaker, microphone, keypad, keyboard, mouse, touchpad, and other user communications devices, components or systems as known in the art.

Telemedicine booth 200 may use medical parameters capture system 204 to gather one or more of a user's current medical parameters such as for example pulse, blood pressure, or body temperature. To gather the user's medical parameters, medical parameters capture system 204 may include one or more devices or instruments for capture or recording that may be operated by a user with or without guidance or instructions provided via for example user interface 202 or directly by the one or more devices. These devices may include for example a thermometer, weight scale, a blood pressure reader, infra-red imager, vibration sensors, oxygen or carbon dioxide sensors, ECG monitoring device, dermatological camera, pulse oximeter, electronic stethoscope, ultrasound transceiver, and other sensors.

In some embodiments, one or more of the devices in medical parameters capture system 204 may be disposable or single-use, or may require a disposable part such as for example a cover for a thermometer for proper or sanitary operation. Disposable parts or disposables may be stored and supplied directly to the device or to the user by disposables supply 206. After usage, these disposables may require a sanitary disposal device such as e.g. disposal system 208. Disposal system 208 may be or include any appropriate sanitary receptacle or storage device for proper disposal of the medical disposables provided by disposables supply 206. As part of routine operation of telemedicine booth 110, disposables supply 206 and disposal system 208 may require periodic replenishment and emptying respectively. In some embodiments, the telemedicine booth 200 may measure the quantity of disposable parts remaining in the disposables supply 206 and/or the space remaining in disposal system 208. Indications of the remaining quantity or quantities and/or space may be transmitted remotely to service personnel to facilitate timely replenishment of disposable parts and/or emptying of disposal system 208.

To establish a communications link between telemedicine booth 200 and a routing agent such as routing agent 120, telemedicine booth 200 may include a communications system 210. Communications system 210 may be connected to user interface 202 and medical parameters capture system 204 and other components or systems of telemedicine booth 200 and may include appropriate equipment for the transmission and reception of user data, audio and video signals as known in the art. Communications system 210 may be implemented using for example a transmitter, a transceiver, or a transmitter-receiver, or one or more units able to perform separate or integrated functions of transmitting and/or receiving communication signals, blocks, frames, transmission streams, packets, messages and/or data. Communications system 210 may communicate over for example a public network such as a public-switched telephony network and/or the cellular telephone network, a data network such as the Internet, a direct point-to-point fiber link, other wired links, wireless links, and/or satellite links. In some embodiments, communications system 210 may be capable of communicating with a medical service provider such as e.g. medical service provider 130 either directly or through routing agent 120. Furthermore, communications system 210 may be capable of supporting more than one communications link simultaneously.

Payment/authentication system 212 may be or include one or more devices for collecting information identifying the user and payment information. Collecting information identifying the user may be accomplished by for example text entry or audio entry via user interface 202; credit card, identification card, or smart card reader; fingerprint or other biometric sensor; and other collection devices known in the art. In some embodiments, payment/authentication system 212 may use communication system 210 and communication link 160 to connect to database 125 to retrieve a user's records for user authentication or authorization. Payment authorization techniques are well known in the art and may include a separate link such as for example to financial service provider, e.g. a credit card issuing bank. Authenticating or verifying a user's identity and validating the method of payment may occur prior to telemedicine booth 200 establishing a communications link to a routing agent.

During a medical consultation, a medical service provider may prescribe a sample or other sized portion of a medicine to be dispensed in telemedicine booth 200 by medicine dispenser 214. The dispensed medicine may be or include one or more over-the-counter, non-controlled substance medicines such as aspirin. Additionally or alternatively, medicine dispenser 214 may be configured to dispense a limited set of prescription medicines when directed to do so by an appropriately licensed medical service provider. The medication dispenser 214 may be located outside the telemedicine booth 200, such as in a separate cabinet on a nearby wall.

A medical service provider may prescribe a controlled substance medicine not available in medicine dispenser 214 or may provide written care instructions for the user. In these instances, a medical service provider may send a prescription or set of instructions to printer 216 for printing. Printer 216 may be a printing device known in the art for printing documents such as, e.g. general instructions, prescriptions, or receipts. In some embodiments, printer 216 may print on plain paper or one or more forms as appropriate for the prescription or instructions. Printer 216 may also be used to print other documents. In some embodiments, the communications system 210 may send an indication to service personnel that printer 216 needs replenishment.

Figure 3:
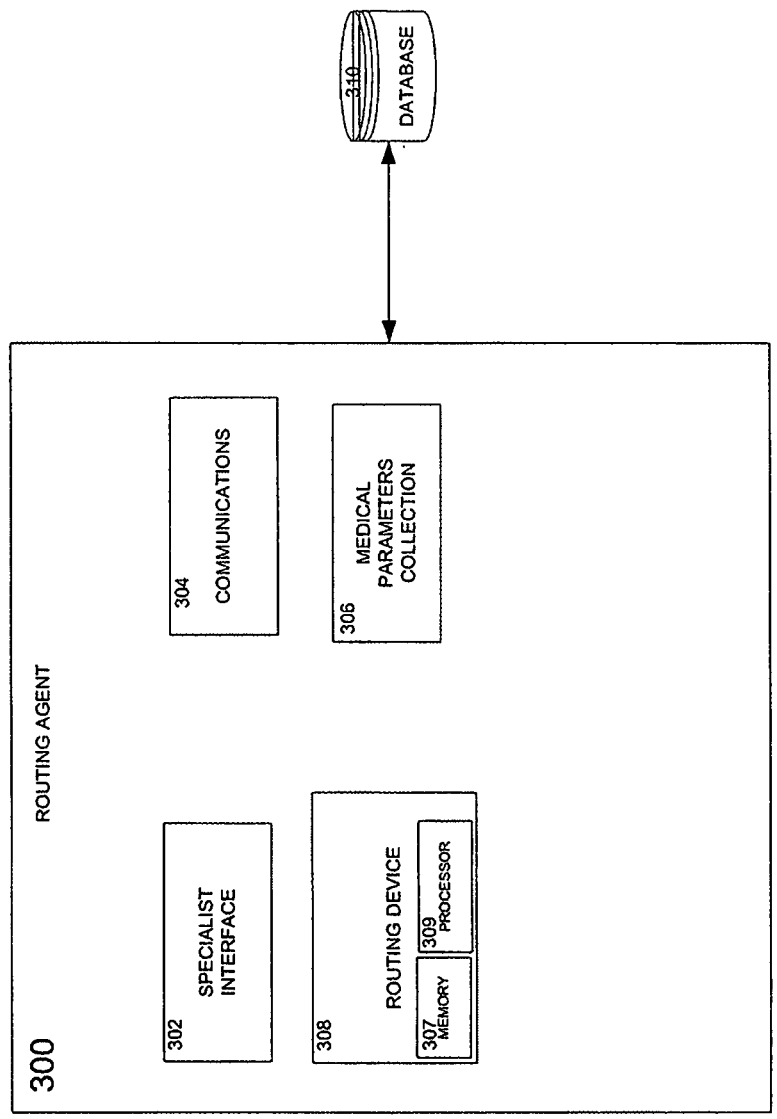
FIG. 3 is a schematic illustration of a routing agent according to an embodiment of the invention.

Reference is now made to FIG. 3, depicting a routing agent according to an embodiment of the invention. Routing agent 300 may be a call center or other intermediary agent for connecting a user in a telemedicine booth with an appropriate medical service provider. Routing agent 300 may include a specialist interface 302, a communications system 304, medical parameters collection system 306, and a routing device 308 which may include a memory 307 and a processor 309.

In some embodiments, routing agent 300 may require staffing for operation and may include a specialist interface 302 for a call or routing specialist who may or may not be a licensed medical professional. Specialist interface 302 may be or include a terminal, telephone and/or other communications equipment for call specialists known in the art. Alternatively, routing agent 300 may be fully automated.

Routing agent 300 may use communications system 304 to connect with telemedicine booth 110 and a medical service provider 130. In some embodiments, communications system 304 may be capable of establishing separate communications links for telemedicine booth 110 and medical service provider 130 and combining them in a conferencing configuration. Communications system 304 may be capable of establishing a direct link between medical service provider 130 and telemedicine booth 110. Communications system 304 may be connected to specialist interface 302 and medical parameters collection system 306 and other components or systems of routing agent 300 and may include appropriate equipment for the transmission and reception of user data, audio and video signals. Communications system 304 may be implemented using for example a transmitter, a transceiver, or a transmitter-receiver, or one or more units able to perform separate or integrated functions of transmitting and/or receiving communication signals, blocks, frames, transmission streams, packets, messages and/or data. Communications system 304 may communicate over for example a public network such as a public-switched telephony network (and/or a cellular telephone network), a data network such as the Internet, a direct point-to-point fiber link, other wired links, wireless links, and/or satellite links. Furthermore, communications system 304 may be capable of supporting more than one communications link simultaneously.

Medical parameters collection system 306 may be or include a computerized device or system for receiving medical parameters collected by a telemedicine booth such as for example telemedicine booth 200. In some embodiments, medical parameters collection system 306 may interact with medical parameters capture system 204 during the process of capturing a user's medical parameters either under the control of a call routing specialist, semi-autonomously, or autonomously. Once the medical parameters are transferred to routing agent 300, they may be stored in a database such as e.g. database 125 or other memory unit (not shown). These medical parameters may later be sent to a medical service provider for use in the consultation process.

Routing device 308 may be a computerized system or device for receiving a number of inputs regarding a user and available medical service providers and matching one or more medical service providers to the user for a medical consultation. The matching process may be performed by an algorithm or other systematic process employing a number of criteria as parameters; scoring, rating, or prioritizing the parameters; and determining one or more medical service providers with the highest scores or ratings. The various inputs required for the determination may be received by routing device 308 from telemedicine booth 110, by direct entry of a call specialist at specialist interface 302, and/or from one or more databases 125.

The inputs regarding the user may include one or more of the user's identity; location; medical history as retrieved from a database 125; current medical parameters, e.g. body vital signs and symptoms, including those captured by telemedicine booth 110 and described by the user; preferences as to medical service provider such as e.g. gender or first language; prior ratings of medical service providers; contracted for service level; and payment budget or account balance. Other user inputs may also be included.

Inputs regarding medical service providers may include one or more of current location, licenses or certifications in the state or country where the user resides or is currently located, availability, personal characteristics such as e.g. gender or language skills, prior experience with the patient, medical specialty, degree of expertise or licensing, prior ratings, and fees for providing a medical consultation. Other medical service provider inputs may also be included.

The routing algorithm or process may rate or score these inputs and combine them in a weighted averaging or scoreboarding or other such calculating process as known in the art for optimizing a match. In some embodiments, the routing algorithm may interpret these criteria as either location based constraints or quality of service constraints. Examples of location based constraints may for example include a user's location, a user's symptoms, a medical service provider's location, and a medical service provider's area of expertise. Examples of quality of service constraints may include for example severity of a user's symptoms as they relate to a level of urgency, duration of a user's waiting time for service, a user's service plan level, a user's willingness to pay more for faster service, and a user's preferences such as e.g. ratings, gender preference, language, and the like. For both types of constraints, a prioritization scheme may be used that may assign higher weighting or more points to some constraints over others such as for example severity of symptoms. Other constraints may be used.

In some embodiments, routing device 308 may be configured to match according to different priorities with different point values assigned to different inputs. For example, in some instances the shortest wait time may be more valued than medical service provider rating or preference. Alternatively, in some instances, routing device 308 may be configured to assign users to the lowest cost medical service provider as the highest priority. Other prioritization schemes may also be used.

Memory unit 309 may include, for example, a Random Access Memory, a Read Only Memory, a Dynamic RAM, a volatile memory, a non-volatile memory, a cache memory, a buffer, a short term memory unit, a long term memory unit, or other suitable memory or storage units. Memory unit 309 may, for example, store data received by routing device 308 such as e.g. user inputs and medical service provider inputs, and/or store other data necessary for carrying out routing operations.

Processor 309 may include, for example, a Central Processing Unit (CPU), a Digital Signal Processor (DSP), a microprocessor, a controller, a chip, a microchip, an Integrated Circuit (IC), or any other suitable multi-purpose or specific processor or controller. Processor 120 may, for example, process data received by routing device 308, and/or perform calculations or other operations in accordance with an embodiment of the invention described herein.

Figure 4:
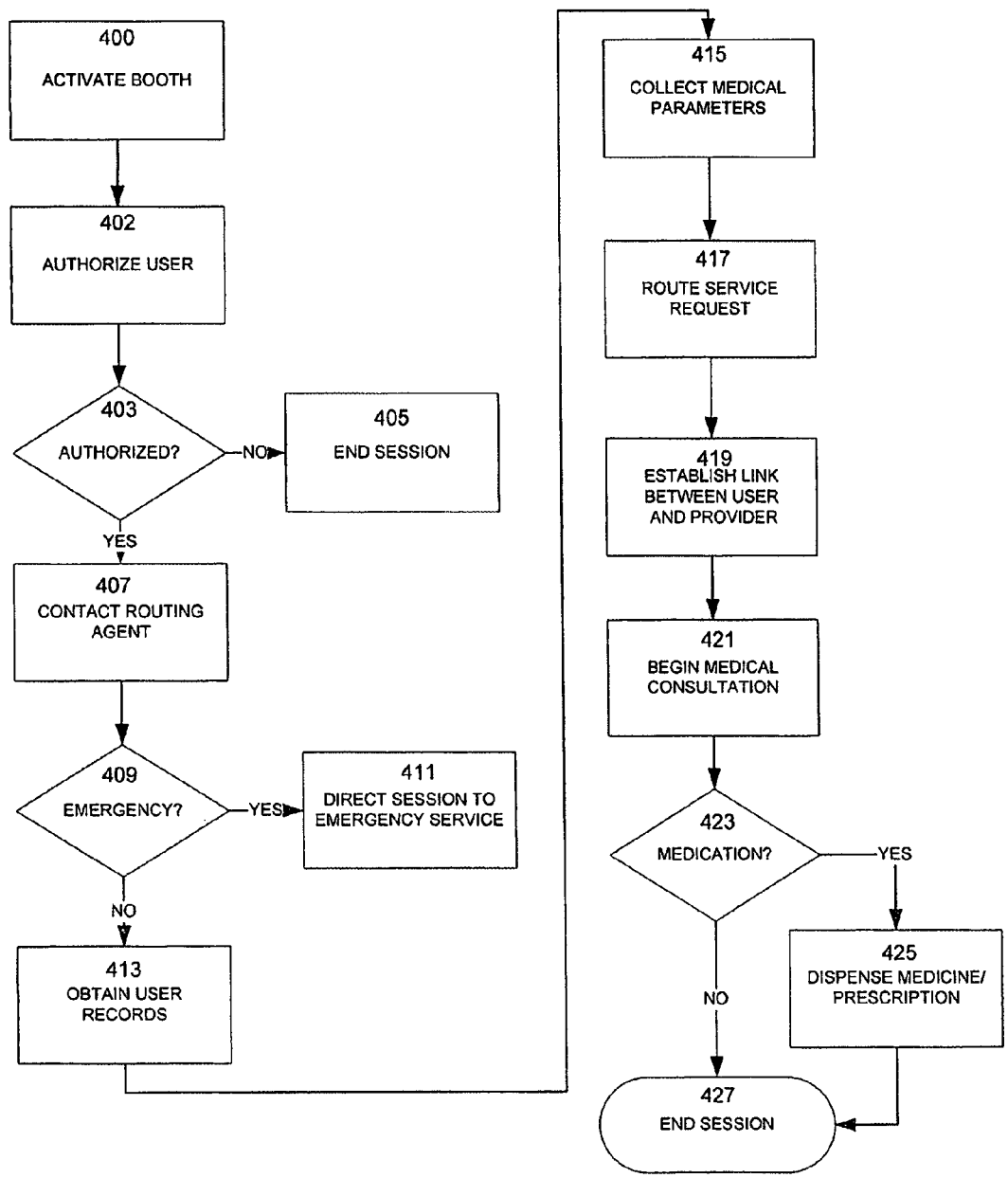
FIG. 4 is a flowchart of a method for routing a medical service request according to an embodiment of the invention.

FIG. 4 is a flowchart of a method according to an embodiment of the invention. Embodiments may be used by, or may be implemented by, for example, system 100 of FIG. 1 or by other suitable combinations of telemedicine booths, routing agents and medical service providers that may be connected by one or more communications networks. As used herein, the process of a user requesting a medical service, being routed to a medical service provider, and having a medical consultation with a medical service provider may be referred to herein as for example a session A user having a request for medical services may begin the session by entering or accessing a telemedicine station or booth such as e.g. booth 110 and activating the booth in operation 400. Booth activation may be triggered upon entry of the user or by closing a door of the booth or other techniques and may include activating a user interface such as user interface 202. User interface 202 may prompt the user for his identity and/or payment information in operation 401. Additionally, a user may be required to produce evidence of membership in a healthcare service plan such as for example a health maintenance organization (HMO). In some embodiments, user may be prompted by user interface 202 to slide a membership card, credit card, or smart card in a card reader. In some embodiments, telemedicine booth 110 may contact a routing agent such as routing agent 120 via a communications link such as communications link 140, a database such as database 125 through communications link 160, or other provider for verify a user's identity and payment information.

If a user's identity is not confirmed and/or a payment type is not approved, telemedicine booth 110 may end the session in operation 405. If a user's identity or membership is verified and payment approved (operation 403), telemedicine booth 110 may, in operation 407, contact a routing agent such as routing agent 120 via a communications link such as link 140. In some embodiments, the routing agent may be operated by a call specialist using an interface such as specialist interface 302. The user and the call specialist may be able to communicate over communication link 140 verbally, by text entry, video display and other interactive systems known in the art. In other embodiments a call specialist need not be used.

In operation 409, the call specialist may determine the user's request for medical service is an emergency or the medical condition requires immediate attention. If the request is an emergency, the user may be directed an emergency medical service provider in operation 411 as part of the session or alternatively the session may end.

If the request is not an emergency, the session may continue with operation 413. Routing agent 130 may obtain a user's medical records by retrieving the records from a database, e.g., database 125 and additionally ask the user for further information during the session. Previously stored medical records need not be used and may not be available. The medical records may be used as an input for routing the user's request for medical service and for determining what medical parameters should be collected at telemedicine booth 110.

In operation 415, the call specialist may prompt the user to provide medical parameters from the user's knowledge or by capturing them via for example medical parameters capture system 204. The collection process may be interactive and vary according to the user's status, such as e.g. apparent symptoms and known conditions, reasons for requesting service, and medical history. In some embodiments, the call specialist may guide or instruct the user through the collection process. Additionally or alternatively, user interface 202 may provide some instructions for collection of certain medical parameters such as e.g. blood pressure. The medical parameters captured by medical parameters capture system 204 may be sent over communications link 140 to medical collection system 306 for subsequent use or possible storage in a database 125, memory 307, or other memory unit not shown.

In operation 417 routing agent 120 may route the user's request for medical service to a medical service provider. The routing may be accomplished using a routing device such as e.g. routing device 308 which may be operated by a call specialist at specialist interface 302. Routing may be performed algorithmically using a prioritization scheme that may for example assign a point value to each of a number of user and medical service data as inputs. The output of operation 417 may be one or more medical service providers such as medical service provider 130 who may be available for a medical consultation with a user. Other methods of deciding on a provider may be used.

In operation 419, the call specialist may establish a link between the user at telemedicine booth 110 and medical service provider 130. In some embodiments, the call specialist may confirm the availability of a first medical service provider 130 via communication link 150 before connecting medical service provider to telemedicine booth 110. If the first medical service provider 130 is not available or not willing to accept the medical consultation, routing agent 120 may attempt to contact a second medical service provider 130 as selected by routing device 308.

Once the link between telemedicine booth 110 and medical service provider 130 is established, a medical consultation may begin (operation 421). In some embodiments, after routing agent 130 establishes the link between telemedicine booth 110 and medical service provider 130, the call specialist may disconnect from the session, leaving the user and the medical service provider to continue the consultation. In some embodiments the call specialist may, at the medical services provider's request, re-enter the session to finish or continue the session with the user.

The type of link for the medical consultation may be audio only such as for example a telephone call. Alternatively, the link may allow both audio and visual communications such for example by videoconferencing. In some embodiments, the selection of the type of link may be limited to or determined by what medium is available at telemedicine booth 110 and medical service provider 130. Furthermore, the connection between telemedicine booth 110 and medical service provider 130 may be different than their respective connections to routing agent 130. For example, communications with routing agent 130 may occur via telephone link while communications between telemedicine booth 110 and medical service provider 130 may occur via videoconferencing link.

In operation 421, the medical service provider may determine whether the user requires medicine or supplies (e.g., bandages). If the user requires medicine and that medicine is in-stock at telemedicine booth 110, telemedicine booth 110 may dispense the medicine from a medicine dispenser, e.g. medicine dispenser 214 (operation 423). Alternatively, if the medical service provider requests a prescription for the medicine, a printer 216 at telemedicine booth 110 may print the prescription. In some embodiments, the medical service provider 130 may send the prescription electronically or verbally via telephone to a pharmacy. The pharmacy may be chosen based on proximity to the telemedicine booth 110 or to the user. Additional or alternative operations to dispense or prescribe medicine to the user may also be used.

Once the medical consultation is complete, medical service provider 130 or routing agent 120 may terminate the session in operation 427. Medical service provider may return control of the session to a call specialist at routing agent 130 prior to operation 427. Call specialist may route the request for medical services to a second medical service provider such as e.g. a pharmacy to fill a prescription or to a second, more specialized, medical service provider. Other operations or series of operations may be used. Furthermore, the order or sequence of steps may be modified. For example, some medical parameters may be collected prior to obtaining a user's records and possibly prior to the telemedicine booth contacting the routing agent.

While the invention has been described with respect to a limited number of embodiments, it will be appreciated that many variations, modifications and other applications of the invention may be made. Embodiments of the present invention may include other apparatuses for performing the operations herein. Such apparatuses may integrate the elements discussed, or may comprise alternative components to carry out the same purpose. It will be appreciated by persons skilled in the art that the appended claims are intended to cover all such modifications and changes as fall within the true spirit of the invention.

The invention claimed is:

1. A method comprising:

receiving, at a routing agent for routing medical service requests to medical agents, a request for medical service from a user originating at a telemedicine station;

determining, using a processor at the routing agent, to which medical agent among a plurality of medical agents to route data based on one more routing criteria;

routing the request for medical service to a first medical agent, wherein the first medical agent comprises a doctor, nurse, nurse-practitioner, or dentist;

initiating a communication link between the user and the first medical agent for a first consultation;

receiving, at the routing agent, one or more medical parameters of the user captured by the telemedicine station;

transferring the one or more medical parameters to the first medical agent;

requesting, at the routing agent, a medical record of the user from a database;

transferring the medical record to, the first medical agent;

terminating the communication link between the user and the first medical agent;

routing the request for medical service to a second medical agent based on a referral received from the first medical agent during the first consultation and based on a proximity of the second medical agent to the telemedicine station; and initiating a communicating link between the user and the second medical agent, wherein the second medical agent comprises a pharmaceutical service provider.

2. The method of claim 1 wherein the one or more routing criteria comprise:

a location based indicator, a quality of service indicator, an availability and medical specialty of the medial service provider, or any combination thereof.

3. The method of claim 2, further comprising transmitting a control signal from the routing agent to a system of the telemedicine station, the system configured to capture the one or more medical parameters of the user.

* * * * *